(12) United States Patent
Sadik et al.

(10) Patent No.: US 7,708,944 B1
(45) Date of Patent: May 4, 2010

(54) ULTRA-SENSITIVE, PORTABLE CAPILLARY SENSOR

(75) Inventors: Omowunmi A. Sadik, Vestal, NY (US); Jason Karasinski, Forty Fort, PA (US)

(73) Assignee: Research Foundation of State University of New York, Binghamton, NY (US)

( * ) Notice: Subject to any disclaimer, the term of this patent is extended or adjusted under 35 U.S.C. 154(b) by 319 days.

(21) Appl. No.: 11/451,842

(22) Filed: Jun. 13, 2006

(51) Int. Cl.
*G01N 21/00* (2006.01)
(52) U.S. Cl. .................. 422/55; 436/518; 436/524; 436/164; 436/172; 422/50; 422/61; 422/68.1; 422/82.05; 422/82.08; 422/57; 435/7.1; 435/283.1; 435/287.2; 435/288.7
(58) Field of Classification Search .................. 422/50, 422/61, 68.1, 82.05, 82.08, 55, 57, 6, 1; 436/7.1, 436/283.1, 287.1, 287.2, 288.7, 518, 524; 436/164, 172; 435/7.1, 283.1, 287.1, 287.2, 435/288.7
See application file for complete search history.

(56) References Cited

U.S. PATENT DOCUMENTS

| | | | | |
|---|---|---|---|---|
| 5,011,608 A | * | 4/1991 | Damjanovic | 210/656 |
| 5,205,291 A | * | 4/1993 | Potter | 600/431 |
| 5,281,825 A | * | 1/1994 | Berndt et al. | 250/458.1 |
| 5,293,210 A | * | 3/1994 | Berndt | 356/39 |
| 5,395,502 A | * | 3/1995 | Pawliszyn | 204/603 |
| 5,503,994 A | * | 4/1996 | Shear et al. | 436/90 |
| 5,610,405 A | * | 3/1997 | Inushima et al. | 250/372 |
| 6,020,207 A | * | 2/2000 | Liu | 436/164 |
| 6,020,209 A | * | 2/2000 | Narang et al. | 436/514 |
| 6,258,606 B1 | | 7/2001 | Kovacs | |
| 6,277,627 B1 | | 8/2001 | Hellinga | |
| 6,294,392 B1 | | 9/2001 | Kuhr et al. | |
| 6,767,733 B1 | | 7/2004 | Green | |
| 6,835,946 B2 | * | 12/2004 | Ogura | 250/584 |
| 6,929,945 B2 | * | 8/2005 | Aravanis et al. | 435/288.5 |

\* cited by examiner

*Primary Examiner*—Melanie J. Yu
(74) *Attorney, Agent, or Firm*—Nixon Peabody LLP

(57) ABSTRACT

A portable, lightweight, rugged, easy-to-operate biosensor useful for rapidly detecting cells, viruses, antibodies, and other proteins. A capillary tube has a capture antibody immobilized on its interior surface. The specific capture antibody is selected based upon a desired target analyte to be detected. A sample potentially containing the target antigen is introduced into the capillary tube. Thereafter, a second antibody labeled with a fluorescent dye is introduced. Upon excitation by electromagnetic energy, typically supplied by a laser, the fluorescence of the sample is captured and analyzed. The apparatus is extremely compact and rugged making it ideal for field use. In addition, accurate results may be obtained by relatively unskilled operators directly from a self-contained readout. Optionally, an external device (e.g., a computer) may be connected to the apparatus via an optional interface. The analysis time provided by the biosensor system of the invention is shorter than has heretofore been possible.

21 Claims, 4 Drawing Sheets

ULTRA-SENSITIVE, PORTABLE CAPILLARY SENSOR

FUNDED RESEARCH

This work is supported in part by Grant Number RF 1033728 from the United States Environmental Protection Agency (USEPA) and IEEC/National Science Foundation/CAT Grant No. 1041429. The Government may have certain rights in this invention.

FIELD OF THE INVENTION

The present invention relates to biosensors and, more particularly to a portable, rugged), relatively inexpensive, biosensor system capable of providing rapid analysis results.

BACKGROUND OF THE INVENTION

Biosensors are devices that typically use biological molecules to detect other biological molecules or chemical substances.

Specific and/or selective binding interactions with one or more biomolecules ("ligands") such as peptides, proteins, enzymes, antibodies, receptors, nucleic acids, aptamers, or the like detect one or more target molecules ("analytes"). Binding of the target molecule to the ligand results in a signal that can be used to detect or quantify the analyte present in a sample. The detector molecules are connected in some way to a sensor that can be monitored by a computer or similar mechanism. Biosensors may use a monoclonal antibody to detect an antigen, or a small synthetic DNA molecule called an oligodeoxyribo-nucleotide to detect DNA.

There is a critical demand for a rapid, simple, cost-effective technique for screening samples, such as blood or other clinical samples, for the presence of biomolecules, including polynucleotides, polypeptides, etc. Specifically, the detection of cells, viruses, spores, antibodies, pathogens, or other proteins is considered important in diagnosing and treating diseases. Such detection is also useful for detecting and quantifying such molecules in pathological and forensic samples.

A wide variety of biosensors of different designs is known to those of skill in the art. Such biosensors are designed for use in clinical research laboratories or similar facilities, but tend to be very bulky, expensive, and relatively fragile. Such biosensor systems are typically complex and require highly trained operators to obtain accurate analysis results. Portable biosensor systems based on immunoassays using the optical waveguide as a platform have become an attractive area in sensor research due to the availability of a wide variety of low cost, low power consuming components and bright photostable fluorophores.

DISCUSSION OF THE RELATED ART

U.S. Pat. No. 6,258,606 for MULTIPLEXED ACTIVE BIOLOGIC ARRAY, issued Jul. 10, 2001 to Gregory T. A. Kovacs teaches a biologic electrode array which is coupled to suitable electronic circuits (e.g., sample and hold circuits) and packaged on a single semiconductor chip. The KOVACS chip allows a variety of protein or nucleic acid biomolecules to be attached to specific locations on the semiconductor chip. The biomolecules are exposed to samples; binding of various analytes to specific chip locations may be detected, for example, by fluorescence spectroscopy. However, an apparatus built using the KOVACS chip is typically too bulky for field use.

U.S. Pat. No. 6,277,627 for BIOSENSOR, issued Aug. 21, 2001 to Homme W. Helling a teaches a biosensor based on a genetically engineered glucose molecule (i.e., glucose binding protein) that forms environmentally sensitive reporter groups. The HELLINGA sensor, however, is limited to detecting glucose or close structural analogs.

U.S. Pat. No. 6,294,392 for SPATIALLY-ENCODED ANALYTE DETECTION, issued Sep. 25, 2001 to Werner G. Kuhr et al. discloses a flow-through microchannel biosensor useful for detecting multiple, diverse analytes. Complementary molecules immobilized in the walls of the microchannel bind the analytes. After initial binding, immobilized complexes are denatured and flow past a downstream detector. The microchannel construction is prone to clogging unless samples are carefully prepared to remove particulate contamination.

U.S. Pat. No. 6,767,733 for PORTABLE BIOSENSOR APPARATUS WITH CONTROLLED FLOW, issued Jul. 27, 2005 to Larry R. Green provides a fluidic cube including a stage, a waveguide, a cube body, a vent cap and a vent cap isolator. The GREEN apparatus allows simultaneous processing of multiple samples for a variety of analytes.

However, none of the forgoing patents, taken individually or in any combination, is seen to anticipate or suggest the portable biosensor system of the present invention that overcomes the these limitations of known prior art systems.

SUMMARY OF THE INVENTION

In accordance with the present invention, there is provided a portable, lightweight, rugged, inexpensive, easy-to-operate biosensor for use in rapidly detecting cells, viruses, antibodies, and other such proteins. A capillary tube has a capture antibody or other ligand immobilized on an interior surface thereof. For simplicity, the term capture antibody is used herein to refer to any suitable capture material or ligand. The specific capture antibody is selected based upon a desired (i.e., target) analyte (e.g., antigen) to be detected. A sample potentially containing the target antigen is introduced into and, optionally, circulated within the capillary tube. Thereafter, a second antibody labeled with a fluorescent dye is introduced. Upon excitation by electromagnetic energy, typically supplied by a laser, the fluorescene of the sample is captured and analyzed. The apparatus of the present invention is extremely compact and rugged making the apparatus ideal for field use. In addition, accurate results may be obtained by relatively unskilled operators directly from a readout forming part of the apparatus or on an external device (e.g., a computer) connected to the apparatus via an optional interface. The analysis time provided by the biosensor system of the invention is also shorter than has heretofore been possible.

It is, therefore, an object of the invention to provide a portable biosensor system that rapidly provides accurate analyses.

It is another object of the invention to provide a portable biosensor system that is both lightweight and rugged.

It is a further object of the invention to provide a portable biosensor system that is battery powered.

It is an additional object of the invention to provide a portable biosensor system that may be used by a relatively unskilled operator to provide accurate measurement.

It is a still further object of the invention to provide a portable biosensor system that uses a self-contained, digital readout to display analysis results.

It is an additional object of the invention to provide a portable biosensor system that incorporates an optional interface for exporting analysis results to an external device for analysis or storage.

It is a further object of the invention to provide a portable biosensor system that uses a capillary treated with a ligand optimized for detection and quantification of a predetermined analyte.

It is yet another object of the invention to provide a portable biosensor system that uses a laser diode as an excitation source.

It is a still further object of the invention to provide a portable biosensor system connectable to a PDA for data collection, wireless monitoring and remote operation.

BRIEF DESCRIPTION OF THE DRAWINGS

A complete understanding of the present invention may be obtained by reference to the accompanying drawings, when considered in conjunction with the subsequent, detailed description, in which.

DETAILED DESCRIPTION OF THE PREFERRED EMBODIMENT

The threat of bioterrorism has spawned a flurry of research focused on developing portable biosensor systems capable of rapidly and sensitively detecting proteins, cells, and other biomarkers. The present invention features a portable biosensor-based detection apparatus using a capillary tube, laser, photodetector and associated electronics to quickly and accurately detect the presence of a specific antigen or other analyte in a sample. The biosensor system of the present invention is a portable capillary biosensor that utilizes fluorescent immunoassays inside a capillary tube (i.e., a capillary) to detect and quantify analytes. The capillary forms a waveguide wherein the sample-containing capillary is illuminated along substantially its entire length. The resulting fluorescent emission is then received (i.e., collected) at the end of the capillary using a photo-detector.

Figure 1:
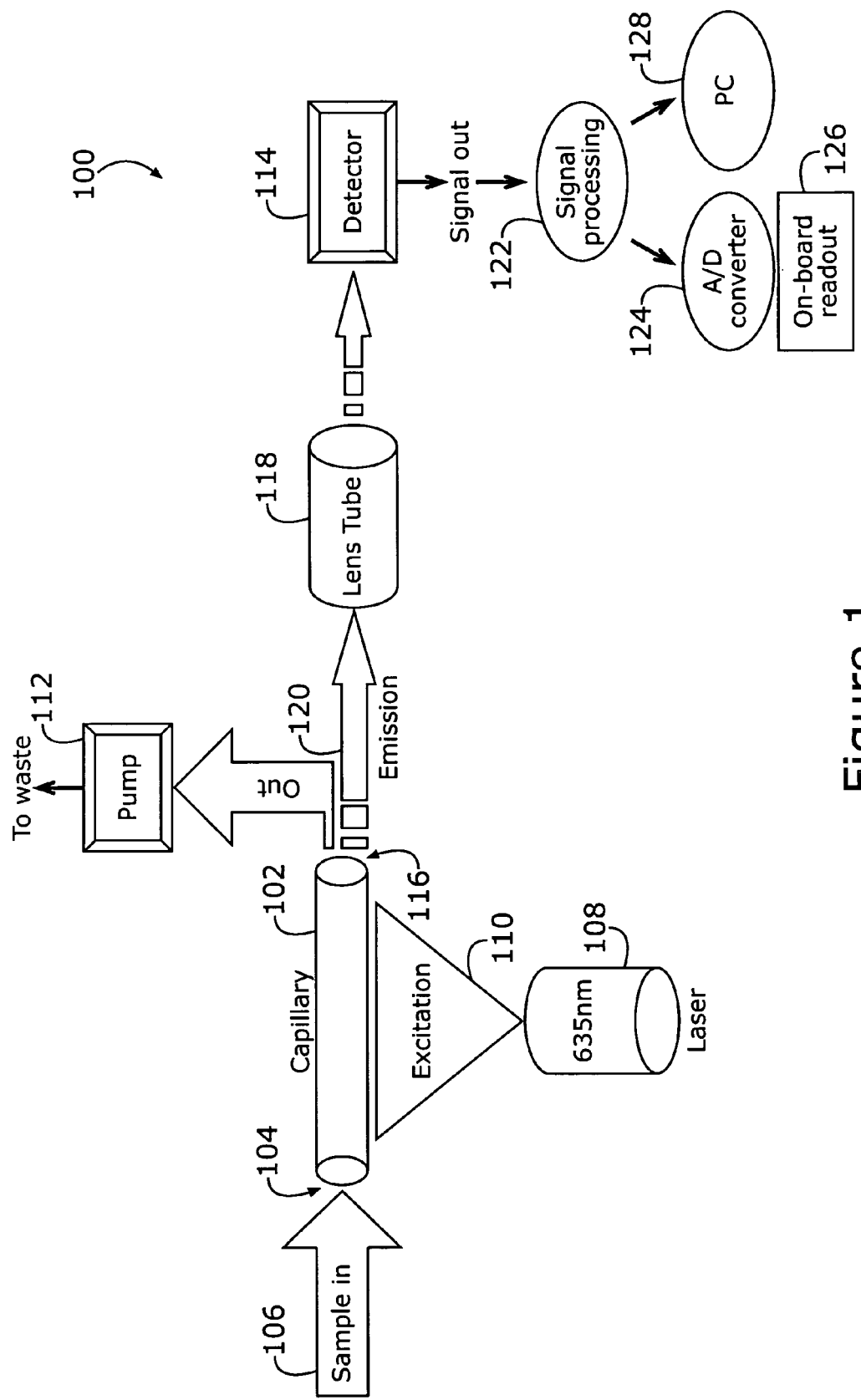
FIG. 1 is a schematic system block diagram of the portable biosensor system of the present invention.

Referring first to FIG. 1, there is shown a schematic, functional block diagram 100 of the portable biosensor apparatus of the invention. A capillary tube 102 has a proximal end 104 where a sample 106 to be analyzed may be introduced. Capillary tube 102 has an inner surface selectively coated with a suitable immobilized antibody or other suitable capture substance Such as RNA, DNA, spores, bacteria, whole cells, aptamers and other ligands. As discussed hereinbelow, the choice of capture antibody is dependent upon the target substance to be detected.

Several forms of waveguides in a variety of formats including glass slides (planar waveguides), microarrays, fiber optics, and capillaries have been used as transduction methods for fluorescent immunoassay. Capillaries offer several unique advantages over other waveguide forms or formats. First, it has been shown that the fluorescence signal accumulates along the length of the capillary 102 while the background noise remains substantially constant. This fact provides lower detection limits (i.e., higher sensitivity) compared to other waveguide forms. Second, the capillary 102 is multifunctional. Once the tube is placed in an instrument 100, the sensing surface does not come into contact with the outside environment and the capillary becomes an integral part of the flow system. Rinsing and incubation steps may be accomplished by simply pumping the required solution into the instrument. In the case where signal amplification using enzyme-linked immunosorbent assay (ELISA) methods are employed, the capillary also becomes the reaction vessel and the product formation therein can be monitored in real time. Capillary sensors can also be coupled with electrophoresis or patterned for multi-analyte detection.

A laser 108 in combination with suitable optics, not shown, illuminates capillary tube 102 along substantially the entire length thereof with excitation energy shown schematically at reference number 110. For purposes of disclosure, a 635 nM wavelength VLM diode laser module having a power output of approximately 15 mW, manufactured by Coherent and supplied as Catalogue No. 0222-021-01 has been found suitable for the application. Laser 108 projects a substantially circular, 1 mm diameter beam. Laser 108 is mounted in a pivot mount, not shown, that also acts as a heat sink. The pivot mount allows the excitation energy 110 to be tightly focused onto the capillary 102 without the need for any intervening, adjustable optical stages. Both 15 mW and 12 mW lasers 108 were evaluated on a bench top instrument by running calibrations with Cy5 dye. The 15 mW laser showed larger voltage changes for the same concentrations of dye, resulting in increased sensitivity. However, the limit of detection of the dye was similar for both lasers in the 40-60 pg/ml range. While Cy5 dye has been chosen for purposes of disclosure, several additional dyes are known to be suitable for use with a 535 nm laser. These include: Cy™5, GE Healthcare Biosciences, Piscataway, N.J.; Alexa Fluor® 647, Molecular Probes, Eugene, Oreg.; TOTO®3 iodide, Molecular Probes, Eugene, Oreg.; SYTO® 17 and SYTO Dyes 59-64, Molecular Probes, Eugene, Oreg.; DyLight™ 647, Pierce, Rockford, Ill.; and DDAO-phosphate 9H-(1,3-dichloro-9,9-dimethylacridin-2-one-7-yl) phosphate, diammonium salt, Molecular Probes, Eugene.

A line-generating lens or grating, not shown, is placed in front of laser 108 to spread the circular output beam into a line of illumination along capillary tube 102. Such an optical component is well known to those of skill in the optical field and is not further described herein. It will be recognized that a number of suitable optical components exist for performing the beam spreading (e.g., line generating) function; the invention is not limited to a line-generating lens or grating. Rather, any optical component suitable for forming a line or field of radiant energy 110 along capillary tube 102 may be used.

A pump 112 is provided to both introduce and evacuate the sample to and from capillary tube 102 and, optionally, in cooperation with other apparatus components, not shown, to circulate the sample within capillary tube 102. In the embodiment chosen for purposes of disclosure, a miniature, variable-speed peristaltic pump 112, such as Model No. SP100V0, pump manufactured by APT, Litchfield, Ill., was utilized. The pump 112 is connected to a 3-way switch, not shown, or other suitable control that permits selective operation of pump 112 at flow rates of approximately 0.18 ml/min (high speed) and 0.4 ml/min (low speed). The faster flow rate has been found useful for performing rinsing steps as described hereinbelow. It will be recognized that other suitable pumps or pumps having different flow rates may be known to those skilled in the art and may be substituted for the APT pump used for purposes of disclosure. The invention is not considered limited to any particular pump or specific flow rates. Rather, the invention covers any and all suitable pumps and/or flow rates.

A photosensor 114 is disposed proximate a distal end 116 of capillary tube 102 via optical arrangement 118. Photosensor 114 monitors the fluorescence of the excited sample 106 within capillary tube 102, shown schematically as emission 120, and generates an electrical signal representative thereof. A photomultiplier tube or other sensitive photosensor may be used. Examples of other photosensors include photodiodes include photodiodes and infrared detectors, for example, Michelson Interferometers.

In the preferred embodiment, optical arrangement 118 and detector (i.e., photosensor) 114 are axially aligned with the central, longitudinal axis of capillary tube 102. In the embodiment chosen for purposes of disclosure, a conventional lens tube 150 (FIG. 2) known to those of skill in the optical arts is used to support and align a pair of plano-convex lenses 152, 154 (FIG. 2) to focus and concentrate emission light 120 at a receiving surface of photo detector 114. It will be recognized that other optical arrangements, likewise, may be used. It will further be recognized that a fiber optical coupling could be inserted between distal end 116 of capillary tube 102 and other optical arrangement 118 or photosensor 114. Consequently, the invention is not limited to the particular photosensor 114, optical arrangement 118, or placement of the photosensor relative to capillary tube 102 chosen for purposes of disclosure. Rather, the invention covers any and all suitable photosensors 114, optical arrangements 118, and relative positions of photosensors 114 to capillary tube 102.

Signal processing electronics 122 is operatively connected to photosensor 114 and receives an electrical signal therefrom. An analog-to-digital (A/D) converter and associated circuitry 124 is used to drive an on-board display or readout 126 where quantitative/qualitative information regarding a sample being tested is displayed. In alternate embodiments, an optional interface 128 may be provided to allow attachment of a computer (e.g., a notebook computer, PDA, etc.) or other external device useful for processing, correlating, post analyzing, or otherwise processing and/or storing result data. Such interfacing may be accomplished in a wide variety of ways including, but not limited to, serial and parallel direct connections, infrared communications ports, network (including wireless) connections, proprietary interfaces, and the like. As these interfacing techniques are considered well known to those of skill in the computer arts, they are not further described herein. The invention is seen to encompass any viable communication strategy.

In operation, reagents, not shown, are introduced into capillary tube 102 adjacent proximal end 104 where they interact with the immobilized antibody 162 (FIG. 3) or other suitable capture substance coated upon the inner surface 160 thereof. Once the target analyte is captured, a fluorescent labeled antibody, a fluorescent labeled avidin, or a fluorescent ELISA using an avidin/alkaline phosphatase complex is introduced into capillary tube 102. For fluorescence detection, Alexa-Fluor 647 is preferred due to its improved performance over Cy-5 when used to label tracer antibodies for sandwich immunoassays. As mentioned hereinabove, other materials may be substituted for Alexa-Fluor 647. Also any other similar, suitable substances known to those of skill in the art may be substituted therefor.

Figure 2:
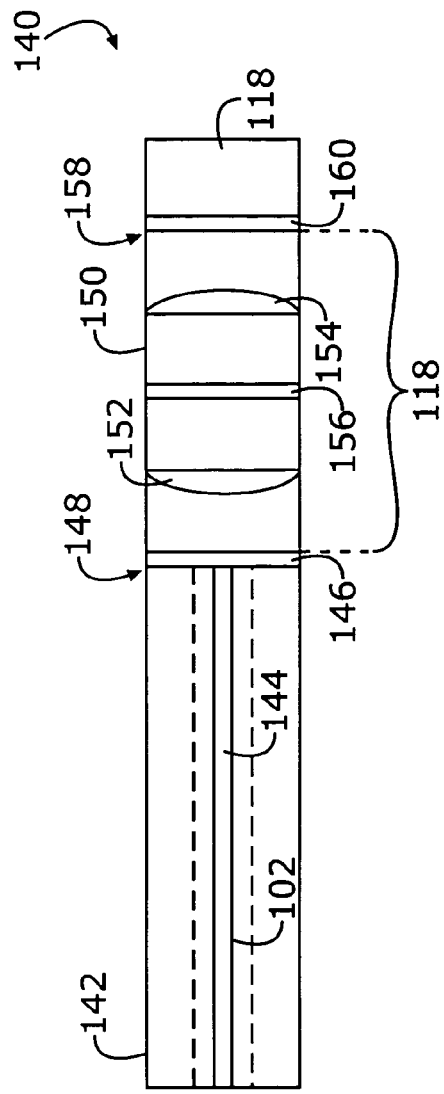
FIG. 2 is side, elevational, schematic view of the capillary tube, optical arrangement, and photosensor of the biosensor system of FIG. 1.

Referring now to FIG. 2, there is shown a side, elevational, schematic view of capillary tube 102 in a support structure, generally at reference number 140. In the embodiment chosen for purposes of disclosure, capillary tube 102 is a fused silica capillary approximately 38 mm long having an inside diameter of approximately 0.7 mm and an outside diameter of approximately 0.85 mm. The capillary tube 102 is available from Polymicro Technologies, Phoenix, Ariz.

Capillary tube 102 is mounted in a custom scaffold 142 that contains a longitudinal window that allows the line laser beam 110 (FIG. 1) to illuminate capillary 102 along substantially the entire length thereof. Emission (e.g., radiation) is collected through a transparent window 146 disposed at a distal end 148 of scaffold 142. In the embodiment chosen for purposes of disclosure, scaffold 142 is formed from polystyrene. Polystyrene was chosen for its weight, rigidity, and ease of machining in constructing prototypes. However, it will be recognized that other lightweight but rigid material such as computer-milled aluminum and Teflon with 70% glass may also be easily substituted for polystyrene.

A stackable lens tube 150, obtained from Thorlabs, Newton, N.J., is abutted to and axially aligned with the transparent window 146. In the embodiment chosen for purposes of disclosure, lens tube 150 is approximately 3 inches long and has a diameter of approximately 1 inch. Lens tube 150 supports optical components, for example a pair of plano-convex lenses 152, 154 and a long-pass interference filter (e.g., a 650 nm low-pass filter 156 obtained from Omega Optical, Brattleboro, Vt.). Lenses 152, 154 and filter 156 form optical arrangement 118 as shown in FIG. 1. The lens tube 150 is threaded on the inside. Retaining rings, not shown, are used to hold the optics 152, 154, 156 in place therein. This arrangement allows the optical components 152, 154, 156 to be optimally distance-adjusted with respect to one another, to the end of capillary tube 102, and to photosensor 114, respectively, and then secured in place within lens tube 150.

Photosensor module (i.e., photodetector) 114 is attached to distal end 158 of lens tube 150 via a custom made Nylon fitting 160. A Catalog No. HC-5784-20 photosensor manufactured by Hamamatsu (Japan) has been found suitable for the application. Nylon fitting 160 has a diameter of approximately 1-inch and a thickness of approximately 0.5 inches. Nylon fitting 160 is secured into lens tube 150 with retaining rings, not shown, and is equipped with mounting screws compatible with photosensor 114. This allows lens tube 150 to be attached to the photosensor module 114 via mating, pre-drilled holes on the front, light-receiving surface thereof.

The photosensor module 114 contains a photomultiplier tube, not shown, a built-in high voltage power supply, and a low noise amplifier that converts the output current from the photomultiplier tube to voltage representative thereof. When compared to a well-known Hamamatsu HC 120 bench top analyzer, it was found that the 5784 photosensor 114 exhibited lower noise than did the HC 120 instrument. However, 5784 photosensor 114 had lower gain resulting in decreased detector sensitivity. The lower sensitivity was overcome somewhat by using a higher power (e.g., 15 mW vs. 12 mW) laser 108 in the portable instrument.

The rigid alignment provided by the sensor platform (i.e., capillary tube 102/scaffold 142) optical arrangement 118, and photodetector 114 typically were found to require no further alignment adjustment after assembly. The arrangement has been found adequate for field use where the system may be exposed to some shock during transportation and use.

Figure 3:
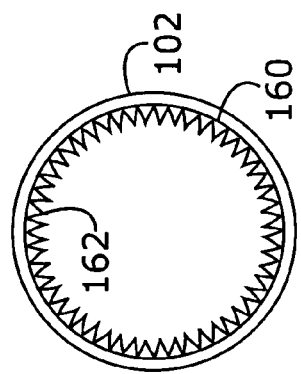
FIG. 3 is a end, cross-sectional view of the capillary tube of the biosensor system of FIG. 1.

Referring now to FIG. 3, there is shown an end, sectional, schematic view of capillary tube 102. The inside surface 160 of capillary tube 102 is coated with capture material (e.g., an immobilized antibody, etc.) 162 as described in detail hereinbelow. Many different materials may be immobilized on interior surface 160 of capillary tube 102. The selection of capture material 162 depends, of course, upon the analyte to be detected and/or quantified. For example, goat anti-mouse IgG, mouse IgG whole molecule, biotinylated goat anti-mouse and the phosphatase substrate para-nitrophenyl phosphate (PNPP) may be utilized as required. The aforementioned materials are available from Pierce Biotech, Rockland, Ill.

The target analyte is captured by immobilized antibody 162 on the inner surface 160 of capillary tube 102 and then detected using a fluorescent labeled antibody, a fluorescent labeled avidin, or a fluorescent ELISA in conjunction with an avidin/alkaline phosphatase complex. For fluorescence detection, Alexa-Fluor 647 was selected due to its reported improved performance over Cy-5 when used to label tracer antibodies for sandwich immunoassays. It will be recognized, however, that a single capture antibody 162 may be used. In alternate embodiments, the system can also be adapted for multi-analyte detection by the use of a patterned capillary tube 102 wherein more than one capture antibody 162 may be applied to surface 160. In still other embodiments, multiple capillary tubes 102, each coated with a different capture antibody 162 and disposed in a parallel arrangement, may be used to detect multiple analytes in a sample.

For purposes of disclosure, three different immunoassay formats using fluorescent labeled proteins, avidin/biotin chemistry, and enzyme linked immunosorbent assays are described. These methods were optimized using mouse IgG as the target antigen. The results of each assay were compared with each other as well as with the results of a conventional colorimetric ELISA assay performed in a 96-well plate.

Capillary tubes 102 were first prepared assuming the desired analyte to be goat anti-mouse IgG by serially interconnecting multiple capillary tubes 102 using Tygon™ tubing. Solutions were drawn into the string of capillary tubes 102 using a plastic syringe, not shown. A syringe having a toluene-resistant plastic plunger and a lure-lock tip were found suitable.

Immobilization of the goat anti-mouse capture antibody was achieved using covalent chemistry well known to those of skill in the art. After a sequence of cleaning steps using approximately 50-50 ratio of methanol/HCl and sulfuric acid, the capillary tubes 102 were incubated under nitrogen with a 2% solution of 3-mercaptopropyl trimethoxy silane in anhydrous toluene. The capillary tubes 102 were then treated with the hetero-bi-functional cross linker (N-[ã-maleimidobutyryloxy]succinimide ester)(GMBS). Goat anti-mouse capture antibodies at a concentration of 10 µg/ml in phosphate buffered saline (PBS) were then attached to the capillary tube 102 via the crosslinker by an overnight, refrigerated incubation.

For direct assays, a 10 µg/ml solution of goat IgG whole molecule was immobilized in place of the anti-goat capture antibody. Before use, the capillary tubes 102 were blocked with a 1 mg/ml solution of BSA. For a direct comparison, conventional colorimetric sandwich ELISA assays were performed using the same antibody-antigen combination as used in the capillary tubes 102. A 96-well micro-titer mouse in pH 9.6 carbonate buffer treated for 2 hours at room temperature was performed. The micro-titer plates were rinsed thrice and blocked with a 10 mg/ml BSA solution in PBS with another 2-hour incubation at room temperature.

After preparation with the capture antibody as described hereinabove, the ELISA plates were exposed to the antigen (mouse IgG) standards for 1 hour followed by a rinse step and an hour exposure to 10 µg/ml solution of biotinylated goat anti-mouse. After another rinse step, the wells were exposed to the avidin/alkaline phosphatase substrate in pH 8.0 Tris buffered saline with 5 mg/ml BSA for 1 hour. The enzyme complex was tittered at ratios of 1:5000, 1:10,000, 1:20,000 and 1:40,000. The PNPP substrate in DEA buffer, pH 9.6, was added to each well and incubated for 20 minutes. Plates were then read at 405 nm on a Biotek Elx800 microplate reader.

Direct binding assays were initially performed using the portable instrument of the present invention to compare the signal generated by an avidin-Alexa Fluor 647 conjugate and an avidin-alkaline phosphatase complex coupled with DDAO-phosphate as a substrate. In this scheme, the mouse IgG was immobilized at a constant concentration in the capillary tube 102 and the goat anti-mouse/biotin (GAMB) was diluted and used as the standard to be detected. For direct ELISA assays, the GAMB standards (prepared in phosphate buffered saline with 1 mg/ml BSA and Tween 20 (PBSTB)) was drawn into the capillary 102 using a plastic syringe and then incubated for approximately 15 minutes.

The capillary 102 was then rinsed with PBSTB and a 1:20,000 solution of the avidin/AP complex in pH 8.0 tris buffered saline with 5.0 mg/ml BSA was added and incubated for approximately 5 minutes. The capillary 102 was then inserted into the instrument and a buffer was flowed therethrough through at a flow rate of approximately 0.19 ml/min. After a few seconds, the inlet was switched over to the substrate (20 µM DDAO in pH 9.8 Tris buffer with 100 mg/L $MgCl_2$). As used herein, the term substrate refers to the molecules used for amplification of immunological reactions commonly used in Enzyme linked Immunosorbent Assay (ELISA). ELISA is considered the "gold standard" for immunological analytical techniques. In an ELISA, an antibody (primary) specific to an antigen (or target species) is immobilized onto a solid support such as a polystyrene plate microwell plate. The antigen, (or target species) specifically binds to the capture antibody. A labeled second antibody (secondary) specifically recognizes another epitope on the antigen (or a site on the target). The secondary antibody is conjugated to an enzyme and doubles up as the detection antibody. The final step of the assay is amplification, which is made possible by the addition of a substrate upon which the enzyme acts with a very high turnover rate giving a detectable product. The endpoint of the enzymatic reaction, typically leads to a colored product that is detected spectrophotometrically. The absorbance is used to quantify the amount of antigen or target species present in the sample.

When the substrate passed into the capillary, the pump 112 was shut off and the enzymatic cleavage of DDAO was allowed to proceed.

For direct assays involving avidin-AF647, the GAMB standards were incubated in the same manner as described hereinabove. However, after the incubation step, the capillary 102 was placed in the potable instrument. Buffer was flowed through the capillary 102 and a baseline voltage was recorded for approximately 20 seconds. A solution of avidin-AF647 (10 µg/ml in PBSTB) was then introduced into capillary tube 102. After the avidin-AF647 solution had entered the capillary tube 102, the pump 112 was switched off and incubation of approximately 5 minutes was allowed. After the incubation period, buffer was reintroduced into capillary tube 102 and the pump 112 was operated at high speed for approximately 30 seconds. Following the buffer rinse, the electrical output signal was recorded with an increase in voltage being indicative of surface bound AF647.

Capillary sandwich fluorescent ELISA assays were performed using the capillaries 102 with immobilized goat anti-mouse IgG. Capillaries 102 were strung onto syringes using Tygon tubing. An incubation sequence having the indicated steps was then performed:

i) incubate with mouse IgG standard;

ii) incubate with GAMB secondary antibody (10 µg/ml); and iii) incubate with avidin-AP complex.

Appropriate rinses were performed between each of the incubation steps by drawing a buffer solution into the syringe, disconnecting the capillaries 102, and discharging the buffer solution. The sequence was repeated two additional times. After the final incubation, the capillary 102 was inserted into the instrument and the DDAO substrate was flowed in as in the direct assay method described hereinabove. For optimization, different incubation times ranging between approximately 5 and 60 minutes, and different titers of the enzyme complex (1:5,000 to 1:30,000) were used. These parameters, in conjunction with controls containing no capture antibody, no antigen or no biotinylated secondary antibody were used to determine an optimum assay. Assays using the avidin-AF647 complex were executed using the following sequence:

i) incubate with mouse IgG standard for 10 minutes;

ii) incubate with GAMB secondary antibody for 5 minutes (10 µg/ml);

iii) insert capillary 102 into instrument and record a baseline;

iv) flow in avidin-AF647 complex and incubate for 5 minutes; and v) rinse for 30 seconds and record signal while flowing buffer at 0.18 ml/min.

Controls used were identical to those described for the fluorescent ELISA hereinabove.

Sandwich assays using the AF-647 labeled goat anti-mouse tracer antibody were performed in a similar fashion. After incubation with the antigen standards for 10 minutes, the capillary 102 was inserted into the instrument. A solution of 10 µg/ml AF-647 labeled goat anti-mouse in PBSTB was introduced into capillary tube 102. The pump 112 was shut off and the antibody was allowed to incubate for various times in the range of between approximately 4 and 15 minutes to optimize the signal to noise ratio. Controls consisted of capillary tubes 102 prepared with no capture antibody as well as blank capillary tubes 102 with no antigen present.

Materials for use in evaluating and/or operating the biosensor system of the present invention are available from several sources. Alexa-Fluor 647 NHS-ester, Alexa Fluor 647-labeled streptavidin and the phosphatase substrate 9H-(1,3-dichloro-9,9-dimethylacridin-2-one-7-yl) phosphate, diammonium salt DDAO-phosphate) were purchased from Molecular Probes, Eugene, Oreg. Goat anti-mouse antibodies to be used as tracers were labeled with a 15-fold molar excess of Alexa-Fluor 647 NHS-ester at pH 8.0 and incubated overnight in the refrigerator. Unbound AF 647 was removed with protein desalting spin columns (Pierce Biotech, Rockland, Ill.) according to the manufacturer's instructions. The dye: protein ratio was determined to be 4.2:1 by measuring the absorbance at 280 and 650 nm on a Hewlett-Packard diode array spectrophotometer and making the calculations according to the manufacturer's instructions. Bovine Serum Albumin (BSA) and alkaline phosphatase labeled avidin were purchased from Sigma, ST. Louis, Mo.

The system of FIG. 1 may be miniaturized for portable applications. It is desirable that such a portable instrument exhibit four important characteristics. First, size and weight should be minimized to create in instrument readily usable in the field. Ideally, all power for the instrument should be supplied by internal batteries, preferably rechargeable batteries. Second, the instrument must be rugged to withstand rough handling to which such an instrument is typically subjected. As the instrument may contain a fragile capillary tube and optical components requiring relatively precise alignment, proper shock mounting of components is required. Third, the instrument should be sensitive to allow precise quantitative/qualitative measurements to be performed in as short an amount of time as possible. Finally, the instrument should be relatively inexpensive.

The prototype used for purposes of disclosure fulfills these four requirements. The prototype exhibits a weight of approximately 33.5 pounds, or 15.4 kg, and is packaged in approximately a 12×4×5 inch volume. It is believed that the size of the instrument may be further reduced, ultimately to the size of a typical PDA or similar hand-held instrument.

Figure 4:
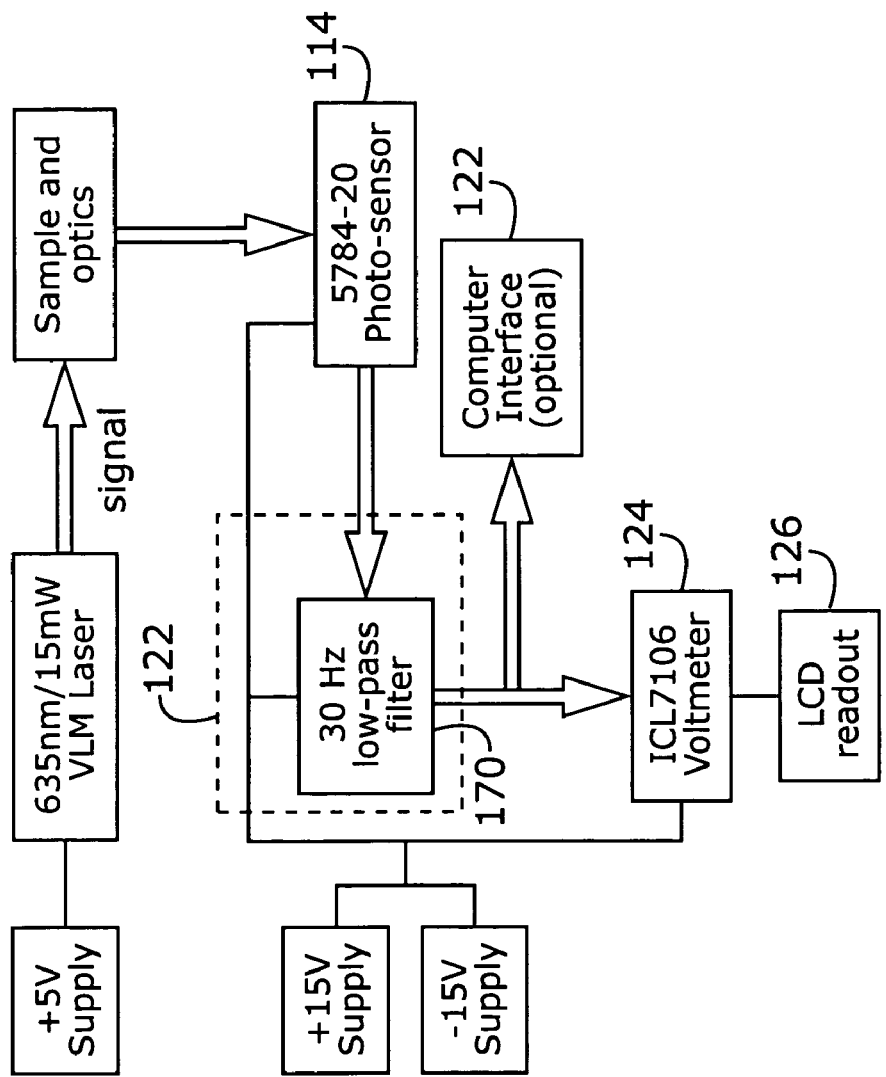
FIG. 4 is a high level, electrical block diagram of the biosensor system of FIG. 1.

Referring now to FIG. 4, there is shown a system block diagram of the portable biosensor of the invention. The electronic signal processing portion 122 consists an low-pass filter 170, an integrating voltmeter 124, a self-contained digital readout 126, and an optional computer interface 122.

An electrical signal output of photosensor 114 is connected to the input of low-pass filter 170. In the embodiment chosen for purposes of disclosure, low-pass filter 170 is implemented as a Butterworth filter consisting of an operational amplifier (op-amp) having an appropriate feedback network to form the desired cut-off frequency and slope. Butterworth filters are well known to those of skill in the electronic design arts and are not further described herein.

Figure 5:
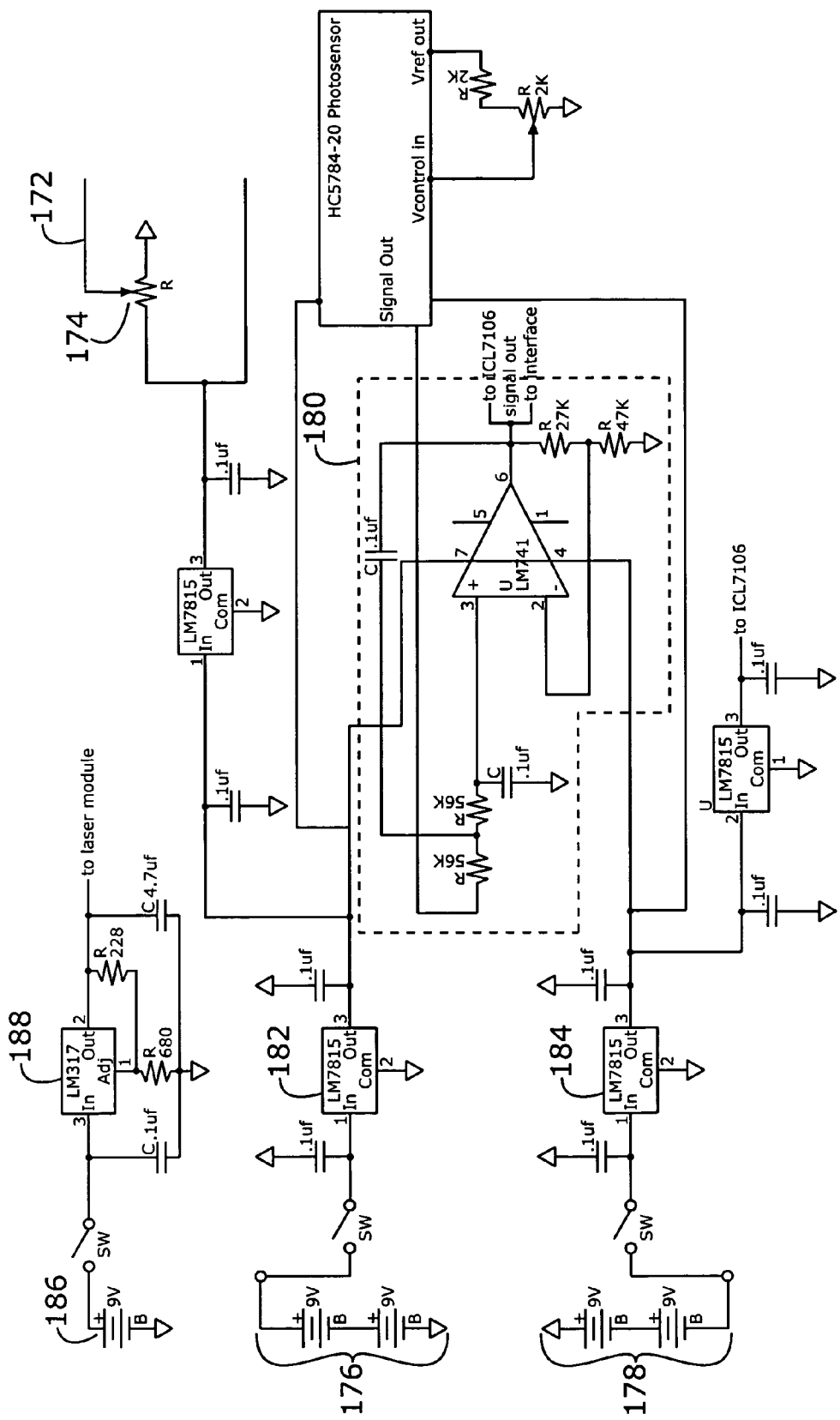
FIG. 5 is an electrical schematic diagram of a preferred embodiment of the biosensor system of FIG. 1.

Referring now also to FIG. 5, there is shown an exemplary circuit diagram of an embodiment of the inventive, portable biosensor system. In the illustrative prototype, an LM-741 op-amp is used. For purposes of disclosure, a filter circuit having an approximately 30 Hz cut-off frequency has been chosen. It will be recognized that other suitable low-pass filter topologies and or implementations may be substituted for the Butterworth filter chosen for purposes of disclosure. Consequently, the invention is not considered limited to any particular filter design. It will be further recognized that circuit designs may be provided without any low-pass filter. The present invention is intended to include such designs as well.

The output of low-pass filter 170 is connected to the input of an A/D converter 124 forming an integrating voltmeter. The output of integrating voltmeter 124 is connected to the input of a digital display device 126 (i.e., a digital readout). Integrating voltmeter 124 may be implemented using an IC7106 analog-to-digital (A/D) converter adapted to directly drive an LCD display device 126. The IC7106 chip accepts an absolute voltage reference (available from the power supply of the portable instrument) using a calibration potentiometer 174 or other suitable arrangement. This allows accurate, absolute voltage measurements to be performed, typically at a rate of approximately 3 readings per second. Reading capability in the range of 0-5 volts has been found satisfactory, even when high concentrations of fluorescent dyes are utilized for an assay. The digital readout 126 of the apparatus has been found to be suitably stable to allow manual recording of readings by an operator of the instrument. A 3.5-digit digital display has been found to be adequate.

The prototype can be operated with a power supply of both plus and minus voltages in the range of approximately 12-15V 176, 178, respectively. Voltage regulators 182, 184 maintain a constant voltage to the circuitry as output voltage from batteries 176, 178 decreases. Series-connected 9-volt batteries have been found suitable to provide voltages 176, 178.

A separate 5-volt power supply consisting of a battery 186 and voltage regulator 188 is used to power laser 108. Battery lifetime is typically not a major concern as both pump 112 and laser 108 are intermittently operated. Although it is possible to power the laser from power supply 176, it is desirable to use a separate power supply 186 or 188 to avoid any electrical transients that might potentially damage laser 108. In addition, as laser 108 requires only a positive voltage, batteries of positive power supply 176 would most likely be discharged more rapidly would than the batteries of negative power supply 178.

The output signal from the low-pass filter 170 is fairly clean and typically does not require complex lock-in amplification or other specialized signal processing. The photosensor module 114, CMOS A/D converter (i.e., integrating voltmeter) 124, filter circuit 180 and LCD display 126 are all driven by the same power supply, typically consisting of four 9-volt batteries. In theory, the power supply can last for a maximum of 70 hours while powering all of the above components. However, if pump 112 and laser 108 (FIG. 1) are run from the same power supply 176, typical battery lifetimes are reduced to approximately 10 hours. As previously stated, either non-rechargeable or rechargeable batteries may be used. Rechargeable batteries are preferable and built-in recharging capability, not shown, may be provided if desired. The low power consuming photosensor module 114 makes possible a biosensor containing two or more of these photosensor modules 114 configured for multi-analyte or multiple sample analysis feasible.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A portable biosensor system, comprising:
   a) a capillary tube extending longitudinally along a major axis between a proximal inlet end and a distal end, said capillary having an interior surface coated with a capture material and forming a waveguide;
   b) a laser disposed proximate and perpendicular to the major axis of said capillary tube and positioned relative to the capillary tube so that energy enters said capillary tube from its exterior along the entire length of said capillary tube to project a line of energy along substantially the entire longitudinal extent of said capillary tube;
   c) a photosensor disposed proximate said distal end of said capillary tube for receiving emissive radiation therefrom, said photosensor generating an output voltage representative of said emissive radiation; and
   d) means for measuring said output voltage.

2. The portable biosensor system as recited in claim 1, wherein said capillary tube comprises means for introducing a fluid into said capillary tube, means for extracting a fluid from said capillary tube, or combinations thereof.

3. The portable biosensor system as recited in claim 1, wherein said capture material comprises a capture antigen.

4. The portable biosensor system as recited in claim 3, wherein said capture antigen comprises at least one material selected from the group consisting of DNA, RNA, whole cells, carbohydrates, and lectins.

5. The portable biosensor system as recited in claim 1, wherein said means for measuring comprises means for displaying a value representative of said voltage.

6. The portable biosensor system as recited in claim 5, wherein said means for measuring said voltage comprises an integrating voltmeter.

7. The portable biosensor system as recited in claim 6, wherein said integrating voltmeter comprises an A/D converter.

8. The portable biosensor system as recited in claim 5, wherein said means for displaying a value comprises a digital display.

9. The portable biosensor system as recited in claim 1, further comprising:
   e) an optical arrangement disposed intermediate said distal end of said capillary tube and said photosensor.

10. The portable biosensor system as recited in claim 9, wherein said optical arrangement comprises at least one lens, an optical filter, and combinations thereof.

11. The portable biosensor system as recited in claim 9, wherein said capillary tube, said optical arrangement, and said photosensor are substantially axially aligned.

12. The portable biosensor system as recited in claim 10, wherein said at least one lens comprises a plano-convex lens.

13. The portable biosensor system as recited in claim 10, wherein said optical filter comprises a low-pass optical filter.

14. The portable biosensor system as recited in claim 1, wherein said photosensor comprises a photodetector assembly, said photodetector assembly comprises a photomultiplier tube, a photodiode, or an infrared detector.

15. The portable biosensor system as recited in claim 6, further comprising:
   e) a low-pass electrical filter disposed intermediate said photosensor and said integrating voltmeter.

16. The portable biosensor system as recited in claim 15, wherein said low-pass filter comprises a Butterworth filter.

17. The portable biosensor system as recited in claim 1, wherein said laser comprises a line-generating lens.

18. The portable biosensor system as recited in claim 1, further comprising:
   e) a computer interface adapted to present a signal representative of said output voltage to a device external to said portable biosensor.

19. The portable biosensor system as recited in claim 2, further comprising:
   e) means for pumping operatively connected to at least one of said means for introducing a fluid into said capillary tube, and said means for extracting a fluid from said capillary tube.

20. The portable biosensor system as recited in claim 19, wherein said means for pumping comprises a multi-speed, peristaltic pump.

21. The portable biosensor system as recited in claim 9, further comprising:
   f) a vibration-isolating mounting structure for supporting at least one of: said capillary tube, said laser, and said photosensor, and said optical arrangement.

* * * * *

UNITED STATES PATENT AND TRADEMARK OFFICE
CERTIFICATE OF CORRECTION

PATENT NO. : 7,708,944 B1
APPLICATION NO. : 11/451842
DATED : May 4, 2010
INVENTOR(S) : Omowunmi A. Sadik Page 1 of 1

It is certified that error appears in the above-identified patent and that said Letters Patent is hereby corrected as shown below:

Col. 1 at lines 6-10, delete "This work is supported in part by Grant Number RF 1033728 from the United States Environmental Protection Agency (USEPA) and IEEC/National Science Foundation/CAT Grant No. 1041429. The Government may have certain rights in this invention.." and insert -- This invention was made with Government support under grant number RD83090610 awarded by United States Environmental Protection Agency (USEPA). The Government has certain rights in this invention. -- in its place.

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,708,944 B1 | |
| APPLICATION NO. | : 11/451842 | |
| DATED | : May 4, 2010 | |
| INVENTOR(S) | : Omowunmi A. Sadik et al. | |

It is certified that error appears in the above-identified patent and that said Letters Patent is hereby corrected as shown below:

Col. 1 at lines 6-10, delete "This invention was made with Government support under grant number RD83090610 awarded by United States Environmental Protection Agency (USEPA). The Government has certain rights in this invention." and insert --This invention was made with government support under RD-83090601-0 awarded by the United States Environmental Protection Agency (USEPA) and DUE9952730 awarded by the National Science Foundation. The U.S. Government has certain rights in the invention.--

Signed and Sealed this
Thirteenth Day of November, 2012

David J. Kappos
*Director of the United States Patent and Trademark Office*